US012565459B2

(12) United States Patent
Nauert et al.

(10) Patent No.: US 12,565,459 B2
(45) Date of Patent: Mar. 3, 2026

(54) NAPHTHA TO ETHANE AND PROPANE UNIT WITH HYDROGEN SLIP

(71) Applicant: UOP LLC, Des Plaines, IL (US)

(72) Inventors: Scott L Nauert, Chicago, IL (US); John J. Senetar, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 18/453,535

(22) Filed: Aug. 22, 2023

(65) Prior Publication Data

US 2024/0158320 A1 May 16, 2024

Related U.S. Application Data

(60) Provisional application No. 63/425,427, filed on Nov. 15, 2022.

(51) Int. Cl.
*C07C 5/327* (2006.01)
(52) U.S. Cl.
CPC .................................... *C07C 5/327* (2013.01)
(58) Field of Classification Search
CPC .......... C07C 5/327; C07C 5/42; C07C 7/005; C07C 7/09; C07C 7/04; C07C 11/04; C07C 11/06
See application file for complete search history.

(56) References Cited

U.S. PATENT DOCUMENTS

| | | |
|---|---|---|
| 10,676,681 B2 | 6/2020 | Ward et al. |
| 11,898,102 B2 | 2/2024 | Xin et al. |
| 2010/0025218 A1 | 2/2010 | Panditrao |
| 2014/0128486 A1 | 5/2014 | Karim et al. |
| 2020/0392418 A1 | 12/2020 | Nesterenko et al. |
| 2023/0357654 A1 | 11/2023 | Funk et al. |

FOREIGN PATENT DOCUMENTS

| | | |
|---|---|---|
| CN | 111807921 A | 10/2020 |
| TW | 201406720 A | 2/2014 |
| WO | 2021174910 A1 | 9/2021 |

OTHER PUBLICATIONS

International Search Report from corresponding PCT application No. PCT/US2023/079373, mailed Mar. 14, 2024.
Written Opinion from corresponding PCT application No. PCT/US2023/079373, mailed Mar. 14, 2024.

*Primary Examiner* — Thuan D Dang

(57) ABSTRACT

A process for making ethylene from a hydrocarbon feed requires separating the hydrocarbon feed comprising ethane, hydrogen, and/or methane and hydrocarbons with 3 or greater carbons into an ethane-rich stream comprising hydrocarbons with 2 or less carbons and a heavy stream comprising hydrocarbons with 3 or more carbons. The ethane-rich stream is passed to a process which produces ethylene. The ethane-rich stream has an ethane to combined hydrogen and methane molar ratio of at least 1.2 and less than or equal to 10.

14 Claims, 7 Drawing Sheets

NAPHTHA TO ETHANE AND PROPANE UNIT WITH HYDROGEN SLIP

RELATED APPLICATIONS

This application claims the benefit of and priority to U.S. Provisional Patent Application No. 63/425,427 filed on Nov. 15, 2022, the entirety of which is incorporated herein by reference.

TECHNICAL FIELD

This invention relates generally to making ethylene from a hydrocarbon feed and processes and apparatuses for making ethylene from a hydrocarbon feed derived from naphtha, and more particularly to separating the hydrocarbon feed into an ethane-rich stream and a propane-rich stream, slipping hydrogen and methane product into the ethane stream to reduce separation cost in a naphtha-to-ethane-and-propane process, and sending the ethane stream containing hydrogen and methane to a process to make ethylene.

BACKGROUND

There is an industry trend towards shifting refining capacity to make increased petrochemicals due to the high value of ethylene and propylene compared to fuels. Naphtha steam cracking is the industry standard for making ethylene and propylene from naphtha, but ethylene plus propylene yields are low—less than 60% and typically less than 50% by weight depending on naphtha composition.

A naphtha-to-ethane-and-propane process (NEP) produces two main products, ethane and propane, which can be fed to a downstream ethane steam cracker and propane dehydrogenation unit to selectively produce ethylene and propylene respectively at higher overall yields than a naphtha steam cracker.

The ethane product from the NEP process contains hydrogen and methane which are expensive to separate. This separation requires either deep refrigeration or a membrane and recycle compressor. Such processes are expensive and, thus, reduce the benefit of higher yields which the NEP process can achieve when ethane and propane are fed to downstream ethane cracker and propane dehydrogenation units.

The present invention is provided to solve the problems discussed above and other problems, and to provide advantages and aspects not provided by prior processes and apparatuses of this type. A full discussion of the features and advantages of the present invention is deferred to the following detailed description, which proceeds with reference to the accompanying drawings.

SUMMARY

One aspect of the present disclosure is directed to a process for making ethylene from a hydrocarbon feed. The process comprises separating the hydrocarbon feed comprising ethane, hydrogen, and/or methane and hydrocarbons with 3 or greater carbons into an ethane-rich stream comprising hydrocarbons with 2 or less carbons and a heavy stream comprising hydrocarbons with 3 or more carbons. The ethane-rich stream is passed to a process which produces ethylene. The ethane-rich stream has an ethane to combined hydrogen and methane molar ratio of at least 1.2 and less than or equal to 10.

Another aspect of the present invention is directed to an apparatus for separating naphtha into ethylene and propylene. The apparatus comprises a source of a first fluid feed to an ethane steam cracker. The first fluid feed comprises a molar ratio of ethane to combined hydrogen and methane in the fluid feed of at least 1.2 and less than or equal to 10. A control device controls the molar ratio.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which.

DETAILED DESCRIPTION

Figure 1:
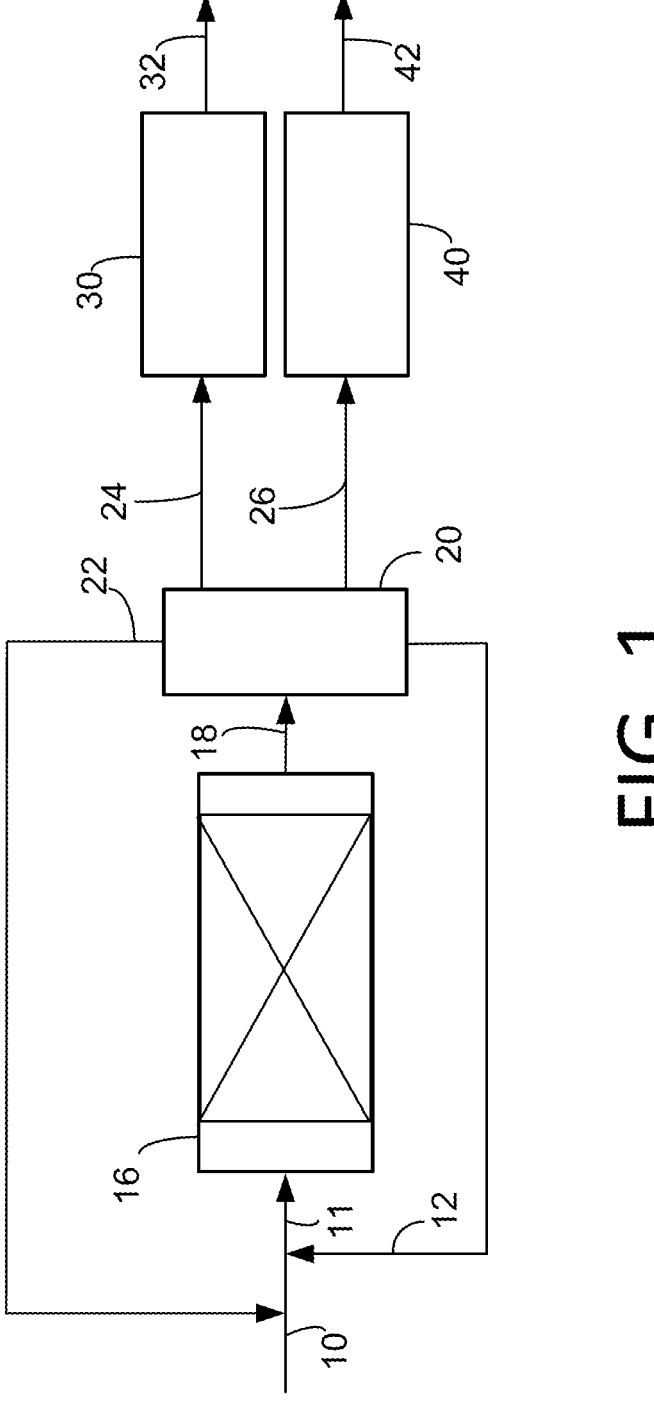
FIG. 1 is a schematic drawing of a process and apparatus of the present disclosure.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

Referring to FIG. 1, a naphtha stream in line 10 may be combined with a hydrogen stream in line 22 and a heavy stream in line 12 to provide a charge stream in line 11, heated and charged to a naphtha to ethane and propane (NEP) reactor 16 to be contacted with an NEP catalyst. NEP reactor block 16 may include multiple reactors in parallel or in series. The naphtha stream may comprise C4 to C12 hydrocarbons preferably having a T10 between about 0-10° C. and about 60° C. and a T90 between about 70 and about 180° C. The naphtha feed stream may comprise olefins, normal paraffins, iso-paraffins, naphthenes, and aromatics. The naphtha stream may be heated to a reaction temperature of between about 300° C. and about 550° C. and preferably between about 325° C. and about 525° C. Naphtha weight space velocity should be between about 0.5 and about 10 hr−1 and preferably between about 1 to about 4 hr−1. Some reactor designs include an inert diluent which increases the overall weight space velocity. But all designs have a naphtha weight space velocity between 1-4 h−1, where naphtha weight space velocity is defined to exclude the inert component. A hydrogen-to-hydrocarbon molar ratio should be about 0.5 to about 5 and a total pressure should be about 0.1 to about 2 MPa (abs). At these conditions, C2-C4 yield is consistently in an excess of 80 wt %, while methane yield is less than about 16 wt %, suitably below about 14 wt % and typically below about 12 wt % and preferably no more than 10% wt %. In a further example, the hydrogen-to-hydrocarbon molar ratio should be typically no more than 5, suitably no more than 3 and preferably no more than 2. Under these conditions, ethane can make up more than 60 wt % of the total C2 to C3 and, for that matter, C2 to C4 produced in the NEP reactor 16. Low hydrogen-to-hydrocarbon ratio promotes desired reaction kinetics which is initiated with dehydrogenation.

The NEP catalyst dehydrogenates the naphtha molecules to their olefinic analog, interconverts the olefins to lighter olefins and hydrogenates the lighter olefins to produce a light paraffin stream comprising ethane and propane. Interconversion can mean that olefins are oligomerized to higher olefins and then these higher olefins are cracked to lower olefins. This chemical mechanism avoids or minimizes hydrogenolysis and pyrolytic cracking reactions which produce methane. Methane is an undesirable by-product that represents an opportunity lost for producing valuable ethane and propane and consumes excessive hydrogen.

The NEP catalyst for converting naphtha to ethane and propane may contain a molecular sieve comprising large or medium pore mouths, comprising 10 or 12 member rings, respectively. Examples of suitable molecular sieves include MFI, MEL, MFI/MEL intergrowth, MTW, TUN, UZM-39, IMF, UZM-44, UZM-54, MWW, UZM-37, UZM-8, UZM-8HS. Examples of suitable molecular sieves further include FER, AHT, AEL (SAPO-11), AFO (SAPO-41), MRE, MFS, EUO-1, TON (ZSM-22), MTT (ZSM-23) and UZM-53. Additional molecular sieves with larger pores include FAU, EMT, FAU/EMT intergrowth, UZM-14, MOR, BEA, UZM-50, MTW, ZSM-12. Additional examples include MSE and UZM-35.

MFI is a suitable NEP catalyst. It will be appreciated that ZSM-5 is an MFI-type aluminosilicate zeolite belonging to the pentasil family of zeolites and having a chemical formula of $NanAlnSi96-nO92·16H2O$ (0<n<10). The ZSM-5 zeolite may comprise a silica-to-alumina molar ratio of 20 to 1000, 20 to 800, 20 to 600, 25 to 400, 25 to 200, or 25 to 80. The ZSM-5 zeolite may comprise a crystal size in the range of 10 to 1500 nm, 20 to 800 nm, 30 to 500, 40 to 400 nm, or 50 to 300 nm.

The NEP catalyst may comprise a bound zeolite. The binder may comprise an oxide of aluminum, silicon, zinc, titanium, zirconium and mixtures of thereof. The binder may comprise a phosphate in the binder or a phosphate of the forenamed oxide binder materials. Preferably, the binder is a silicon oxide. The MFI zeolite may be supported in a silicon oxide containing binder or an alumina containing binder such as aluminum phosphate.

MFI zeolite slurry may be first mixed with a binder in the form of colloidal suspension (sol) and gelling reagent and then dropped into hot oil to make spheres controlled to produce ⅟₈₈-inch to about ⅟₃₂-inch diameter calcined supports. Alternatively, the zeolite may be mixed with a silicon oxide containing binder and extruded to ⅟₃₂ to ¼ inch diameter extrudates. Extrudates may be washed with ammonia to remove sodium ions from the zeolite, dried and calcined to remove the organic structural directing agent (OSDA) from the synthesized zeolite. Optionally, the calcined support may be ammonium-ion exchanged using an ammonium nitrate solution to remove residual sodium ions and dried at about 110° C.

The NEP catalyst comprises a metal on the catalyst. The metal may comprise a transition metal. In a further example, the metal may comprise platinum, palladium, iridium, rhenium, ruthenium and mixtures thereof. The metal may be a noble metal. A modifier metal may also be included on the catalyst. The modifier metal may include tin, germanium, gallium, indium, thallium, zinc, silver and mixtures thereof. The modifier metal should be more concentrated on the binder than on the zeolite. About 0.01 to about 5 wt % of each of the transition metal and the modifier metal may be on the catalyst.

Metal may be incorporated into the binder by evaporative impregnation. A solution of platinum such as tetraamine platinate nitrate or chloroplatinic acid may be contacted with the bound spherical or extrudate supports which have been calcined and ion-exchanged in a rotary evaporator, followed by drying and oxidation.

The NEP catalyst comprises a metal on the bound spherical or extrudate supports of the catalyst. Preferably, more of the metal is on the binder than on the zeolite. At least 60 wt %, suitably at least 70 wt %, preferably at least 80 wt % and most preferably at least 90 wt % of the metal is on the binder. The zeolite and/or the entire NEP catalyst is steamed oxidized to drive the metal off the zeolite. Steaming is preferably effected after the metal is added to the catalyst. The dried, impregnated spherical or extrudate supports may be steam oxidized in air for sufficient time to provide NEP catalysts. Steam oxidation in air at a temperature of about 500° C. to about 650° C. and about 5 mol % to about 30 mol % steam for about 1 to 3 hours may be suitable.

The NEP catalysts must be reduced to activate them for catalyzing the NEP reaction. For example, the catalyst may be reduced in flowing hydrogen at about 500 to about 550° C. for 3 hours before contacting feed.

After paraffin conversion, a light paraffin stream is discharged from the NEP reactor 16 in an effluent line 18. The light paraffin stream may comprise at least 40 wt % ethane or at least 40 wt % propane or at least 70 wt % and preferably at least 80 wt % ethane and propane. The ethane to propane ratio can range from 0.1 to 5. The light paraffin stream can have less than about 16 wt %, suitably less than about 14 wt %, more suitably less than about 12 wt %, preferably less than about 10 wt %, more preferably less than about 9 wt % and most preferably less than about 8 wt % methane.

The presence of sulfur in the NEP reaction does not significantly impact conversion. At least 200 wppm sulfur can be present in the feed without significant impact on conversion. The NEP catalyst may handle as much as 400 and perhaps 500 wppm sulfur without significant impact on conversion.

The light paraffin stream may be cooled and fed to an NEP separation unit 20. The NEP separation unit 20 may be a fractionation column or a series of fractionation columns and other separation units that may separate the light paraffin stream in line 18 into a hydrogen stream in line 22, an ethane stream in line 24, a propane stream in line 26 and the heavy stream in line 12. The NEP separation unit 20 may comprise a demethanizer column that separates the light paraffin stream into a gas stream in an overhead line and a C2+ paraffin stream in a bottoms line. The gas stream may be sent to a hydrogen purification unit such as a PSA unit to recover hydrogen in line 22 for recycle to the NEP reactor 16. Remaining methane from the hydrogen purification unit may be used for fuel gas. The C2+ paraffin stream may then be fed to a deethanizer column to produce the ethane stream in a deethanizer overhead line 24 and a C3+ paraffin stream in a deethanized bottoms line. The C3+ paraffin stream may then be fed to a depropanizer column to produce the propane stream in a depropanizer overhead line 26 and the heavy paraffin stream in the recycle line 12 which may comprise C4+ hydrocarbons. It should be noted that the order of these columns can vary depending on the application. For example, in some cases the deethanizer or depropanizer can be first, and the demethanizer can be placed on either overhead stream. The NEP separation unit 20 may take other forms.

Figure 2:
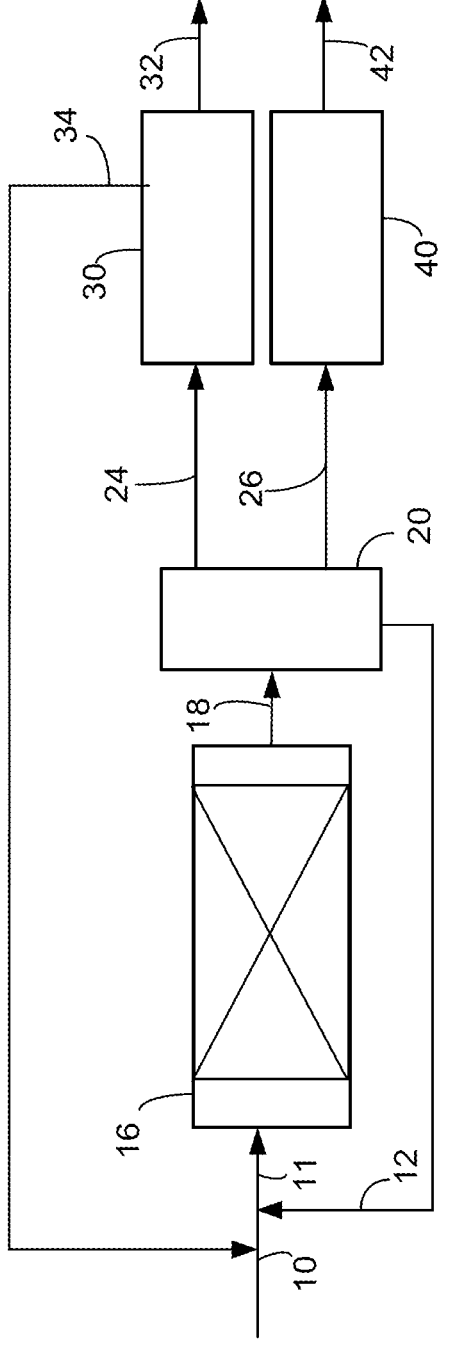
FIG. 2 is a schematic drawing of a process and apparatus of an alternative embodiment of FIG. 1.

For example, the NEP separation unit 20 may omit a demethanizer column and the light paraffin stream in line 18 may feed a deethanizer column which produces a C2– stream in a deethanizer overhead streamline. The C2– overhead stream can be separated in the hydrogen purification unit to recover a hydrogen stream in line 22 while residual ethane and methane from the hydrogen purification unit can comprise or supplement the ethane stream in line 24. The hydrogen purification unit may comprise a membrane unit and the hydrogen recovered from the membrane unit may be further purified in an absorption column before it is recycled to the NEP reactor 16 in line 22. In an additional alternative (see FIG. 2), the C2– stream from the deethanizer column may be charged to an ethylene producing unit 30 in which ethane is converted to ethylene but methane and hydrogen rides through inertly to be recovered in a downstream ethylene recovery unit and sent via line 34 to the NEP reactor 16.

The ethane stream in line 24 may be charged to an ethylene producing unit 30 in which ethane in the ethane stream is converted into ethylene. The ethylene producing unit 30 is a steam cracking unit. The ethane stream in line 24 may be combined with unconverted ethane recycled from the steam cracking unit. The ethane stream in line 24 may be diluted with steam to achieve a desired partial pressure of ethane entering the ethane cracking furnace. The amount of steam mixed with the ethane may preferably be 0.15 kg steam per kg ethane to about 0.5 kg steam per kg ethane. The amount of steam mixed with ethane may be less than the preferred amount if replaced with an equal volume of suitably inert species. According to the principle of the present invention, hydrogen and methane are suitably inert for replacement of steam. The ethane stream in line 24 may be cracked under steam in a furnace to produce a cracked stream including an ethylene stream 32. The ethane stream may be charged to the ethane steam cracking unit in the gas phase. The ethane steam cracking unit may preferably be operated at a temperature of about 750° C. (1382° F.) to about 950° C. (1742° F.). The cracked stream exiting the furnace of the ethane steam cracking unit may be in a superheated state. One or more quench columns, or other devices known in the art, but preferably an oil quench column and/or a water quench column, may be used for quenching or separating the cracked stream into a plurality of cracked streams. The ethane steam cracking unit may further comprise additional distillation columns, amine wash columns, compressors, expanders, etc. to separate the cracked stream into cracked streams-rich in individual light olefins the most predominant of which is the ethylene stream in line 32. The ethylene stream may comprise a yield of at least 75 wt %, preferably at least 80 wt %, ethylene based on the ethane stream in line 24. Among the other components in the cracked stream exiting the ethane steam cracking, ethylene producing unit 30 may be hydrogen, methane, propylene, butene, and pyrolysis gas. Each of these components may be recovered and further processed.

The ethylene stream in line 32 and a propylene stream may be recovered or transported to polymerization plants, chemical plants or exported. A butene stream may be recovered and used to produce plastics or other petrochemicals by processes such as polymerization or exported. Product recovery of at least 50 wt %, typically at least 60 wt % and suitably at least 70 wt % of valuable ethylene, propylene, and butylene products is achievable from the ethane steam cracking unit 30 based on the ethane stream in line 32.

The ethylene producing unit 30 may be an oxidative dehydrogenation (ODH) unit. The ethane stream in line 24 may be charged to the ODH unit. An ethane ODH process is an alternative technology to ethane steam cracking or ethane pyrolysis for the conversion of ethane into ethylene. Ethane ODH involves contacting an ethane feed and an oxygen source in the presence of an ODH catalyst in an ODH reaction zone under conditions to oxidatively dehydrogenate at least a portion of the ethane to produce a product stream comprising ethylene, carbon oxides, water, and unreacted oxygen, acetic acid and other organic acids and unconverted ethane. The oxygen source can be an oxygen containing stream or an oxygen containing material such as a metal oxide. Mixed-metal-oxide catalysts have been found to be effective for oxidative dehydrogenation reactions.

The ODH reactor may use a mixed-metal oxide catalyst and operate at temperatures of about 300 to about 900° C. and produce over 90% ethylene and acetic acid, both useful products. The ODH unit produces the ethylene stream in line 32 along with an acetic acid stream. Ethane oxidative dehydrogenation using the mixed-metal oxide catalysts may be carried out at a temperature from about 300° C. to about 500° C., preferably from about 350° C. to about 450° C. at a pressure of from about 0.1 to about 20 barg, preferably from about 0.1 to about 10 barg, a space velocity of from about 1000 to about 5000 cm3/(gcat·hr), wherein the molar ratio of ethane to oxygen is about 1.5:1 to 2:1 with sufficient inert diluent to achieve safe operating conditions. MoVNbTe-oxide catalysts (and other related materials) with the M1-type structure are believed to be the best catalysts for ethane ODH.

Ethane ODH using a mixed-metal oxide catalysts in which the catalyst is also the oxygen source may be carried out at a temperature from about 600° C. to about 900° C., preferably from about 750° C. to about 850° C. at a pressure of from about 0.1 to about 20 barg, preferably from about 0.1 to about 10 barg, and a gas hourly space velocity of from about 1000 to about 5000 h–1. Mg6MnO8-oxide catalysts (and other related materials) have been identified as preferable materials for ethane ODH processes in which the catalyst is also the oxygen source.

The propane stream in line 26 may be charged to a propylene producing unit 40 in which propane in the propane stream is converted into propylene. The propylene producing unit 40 may be a paraffin dehydrogenation (PDH) unit. PDH catalyst is used in a dehydrogenation reaction process to catalyze the dehydrogenation of paraffins, such as propane. The conditions in the dehydrogenation reactor may include a temperature of about 500 to about 800° C., a pressure of about 40 to about 310 kPa and a catalyst to oil ratio of about 5 to about 100.

The dehydrogenation reaction may be conducted in a fluidized manner such that gas, which may comprise the reactant paraffins with or without a fluidizing inert gas, is distributed to the reactor in a way that lifts the dehydrogenation catalyst in the reactor vessel while catalyzing the dehydrogenation of paraffins. During the catalytic dehydrogenation reaction, coke is deposited on the dehydrogenation catalyst leading to reduction of the activity of the catalyst. The dehydrogenation catalyst must then be regenerated in a regenerator. The regenerator may combust coke from the dehydrogenation catalyst and fuel gas to ensure sufficient enthalpy in the dehydrogenation reactor to promote the endothermic reaction.

The dehydrogenation catalyst selected should minimize cracking reactions and favor dehydrogenation reactions. Suitable catalysts for use herein include an active metal which may be dispersed in a porous inorganic carrier material such as silica, alumina, silica alumina, zirconia, or clay. An example of a catalyst includes alumina or silica-alumina containing gallium, a noble metal, and an alkali or alkaline earth metal.

The catalyst support comprises a carrier material, a binder and an optional filler material to provide physical strength and integrity. The carrier material may include alumina or silica-alumina. Silica sol or alumina sol may be used as the binder. The alumina or silica-alumina generally contains alumina of gamma, theta and/or delta phases. The catalyst support particles may have a nominal diameter of about 20 to about 200 micrometers with the average diameter of about 50 to about 150 micrometers. Preferably, the surface area of the catalyst support is about 85 to about 140 m2/g.

The fluidized dehydrogenation catalyst may comprise a dehydrogenation metal on a support. The dehydrogenation metal may be a one or a combination of transition metals. A noble metal may be a preferred dehydrogenation metal such as platinum or palladium. Gallium is an effective metal for paraffin dehydrogenation. Metals may be deposited on the catalyst support by impregnation or other suitable methods or included in the carrier material or binder during catalyst preparation.

The acid function of the catalyst should be minimized to prevent cracking and favor dehydrogenation. Alkali metals and alkaline earth metals may also be included in the catalyst to attenuate the acidity of the catalyst. Rare earth metals may be included in the catalyst to control the activity of the catalyst. Concentrations of 0.001% to 10 wt % metals may be incorporated into the dehydrogenation catalyst. In the case of the noble metals, it is preferred to use about 10 parts per million (ppm) by weight to about 600 ppm by weight noble metal. More preferably it is preferred to use about 10 to about 100 ppm by weight noble metal. The preferred noble metal is platinum. Gallium should be present in the range of 0.3 wt % to about 3 wt %, preferably about 0.5 wt % to about 2 wt %. Alkali and alkaline earth metals may be present in the range of about 0.05 wt % to about 1 wt %.

Regenerated catalyst may be contacted with the propane stream in line 26 perhaps with a fluidizing gas to lift the propane stream and dehydrogenation catalyst up a riser while dehydrogenation occurs. Above the riser spent dehydrogenation catalyst and propylene product may be separated by a centripetal separation device. Propylene product gas may be quenched with a cooling fluid to prevent over reaction to undesired by-products. Separation of the propylene product may include quench contacting and fractionation to produce a propylene product stream in line 42. Unreacted propane may be recycled to the dehydrogenation reactor and lighter gases may be recycled to the regenerator as fuel gas to be combusted to provide enthalpy for the reaction.

The propylene producing unit may also employ a catalytic moving bed reactor. The reactor section may comprise several radial flow reactors in parallel or series heated by charge and interstage heaters. The propane stream perhaps with added hydrogen flows in each dehydrogenation reactor from a screened center pipe through an annular dehydrogenation catalyst bed to an outer effluent annulus. Flow may be in the reverse fashion. The dehydrogenation catalyst may comprise a noble metal or mixtures thereof, a modifier selected from the group consisting of alkali metals or alkaline-earth metals and mixtures thereof, a component selected from the group consisting of tin, germanium, lead, indium, gallium, thallium, and mixtures thereof, and a porous support forming a catalyst particle. The catalyst support may comprise oil dropped alumina spheres.

Dehydrogenation conditions may include a temperature of from about 400 to about 900° C., a pressure of from about 0.01 to 10 atmospheres absolute, and a liquid hourly space velocity (LHSV) of from about 0.1 to 100 hr–1. The pressure in the dehydrogenation reactor is maintained as low as practicable, consistent with equipment limitations, to maximize chemical equilibrium advantages. Spent dehydrogenation catalyst in the annular catalyst bed may be withdrawn from the bottom of the bed, forwarded to a regenerator to combust coke from the catalyst with air at about 450 to about 600° C. Noble metal on the catalyst may be redispersed by an oxyhalogenation process, dried and returned to the top of the dehydrogenation catalyst bed as regenerated dehydrogenation catalyst.

Dehydrogenation effluent from the propylene producing unit 40 may be cooled, compressed, dried and hydrogen is cryogenically separated from the hydrocarbons with a net gas purity of 85 to 93 mol % hydrogen. Hydrocarbon liquid is selectively hydrogenated to convert diolefins and acetylenes and the hydrocarbon liquid is fractionated in a deethanizer column to remove ethane and propylene is split from propane in a propane-propylene splitter column to provide polymer-grade propylene in line 42. Propane may be recycled as feed to the propylene producing unit 40.

The heavy stream in line 12 which may be taken from a bottom of a depropanizer column may comprise C4+ paraffins. The heavy stream in line 12 may be recycled to the NEP reactor 16 by combination with the paraffin stream in line 10 and the hydrogen-rich stream in line 22 and charged to the NEP reactor in line 11 to produce more ethane and propane.

According to an alternative, the light paraffin stream in line 18 may be separated by the NEP separation unit 20 into a hydrogen stream in line 22, an ethane stream in line 24 and a heavy stream in line 12 as previously described, but the propane stream in line 26 can include isobutane. Here, a propane and isobutane stream in line 26 can be fed to the propylene producing unit 40. The propylene producing unit 40 can be equipped to dehydrogenate propane in the propane and isobutane stream 26 to propylene and isobutane in the propane and isobutane stream in line 26 to isobutylene in the same dehydrogenation reactor(s). The fractionation section from the propylene producing unit 40 may include a depropanizer column downstream of the bottoms line of the propylene-propane splitter column to separate unreacted propane in an overhead from C4 hydrocarbons. An isobutylene-isobutane splitter column in downstream communication with a bottom of the depropanizer column may provide isobutylene in the overhead that can be recovered as product and unreacted isobutane in the splitter bottoms may be returned to the propylene producing unit 40 to be converted to isobutylene.

Unreacted normal C4+ hydrocarbons comprising normal C4 and higher paraffins in the heavy stream 12 may be recycled to be combined with the naphtha stream in the feed line 10 and the hydrogen stream in line 22 and charged to the NEP reactor 16 in line 11.

Figure 3:
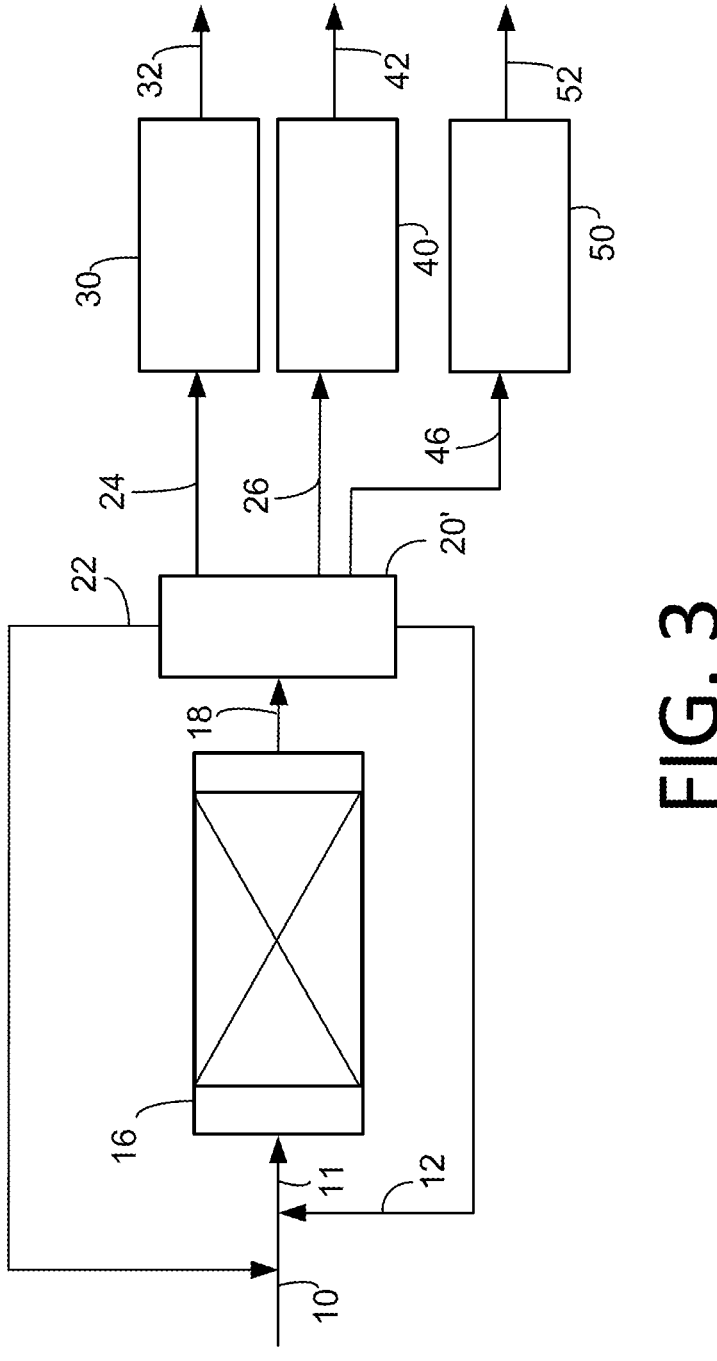
FIG. 3 is a schematic drawing of a process and apparatus of an alternative embodiment of FIG. 1.

FIG. 3 shows an alternative to FIG. 1 which employs a normal butylene conversion unit 50. Elements in FIG. 3 with the same configuration as in FIG. 1 will have the same reference numeral as in FIG. 1. Elements in FIG. 3 which have a different configuration as the corresponding element in FIG. 1 will have the same reference numeral but designated with a prime symbol ('). The configuration and operation of the apparatus of FIG. 3 is essentially the same as in FIG. 1 with the following exceptions.

The NEP separation unit 20' additionally provides a normal butane product stream in line 46 in addition to the hydrogen-rich stream in line 22, the ethane stream in line 24 and the propane and isobutane stream in line 26. The normal butane stream in line 46 may be charged to a normal butylene producing unit 50 for conversion of the normal butane in the normal butane stream to normal butylene. This may be useful in cases in which the propylene producing unit cannot process propane and normal butane in the same dehydrogenation reactor. The normal butylene producing unit may be a dehydrogenation unit as described for the propylene producing unit of FIG. 1.

The normal butylene producing unit may feed a normal butylene stream to a normal butylene-normal butane splitter column. A normal butylene stream in a splitter overhead line may be taken as normal butylene product in line 52 while the unreacted normal butane in the bottoms line may be recycled back to the normal butylene producing unit 50 to be converted to normal butylene.

In some cases, the butylene producing unit 50 may be a butene producing unit that is able to convert both normal butane and isobutane to normal butene and isobutene. In such a case, the line 46 will carry a butane stream which is lean of propane to a butylene producing unit 50 and the propane stream in line 26 will carry a propane stream that is lean in butane to the propylene producing unit. The butene producing unit will produce a butene product stream in line 52 that may comprise isobutene and butene.

The heavy stream in line 12 from the NEP separation unit 20' may comprise a C5+ hydrocarbon stream although it may include C4 hydrocarbons and comprise a C4+ hydrocarbon stream. Unreacted C4+ or C5+ hydrocarbons comprising C4 or C5 and heavier hydrocarbons in the heavy stream 12 may be recycled to be combined with the naphtha stream in the feed line 10 and the hydrogen stream in line 22 and charged to the NEP reactor 16 in line 11.

Figure 4:
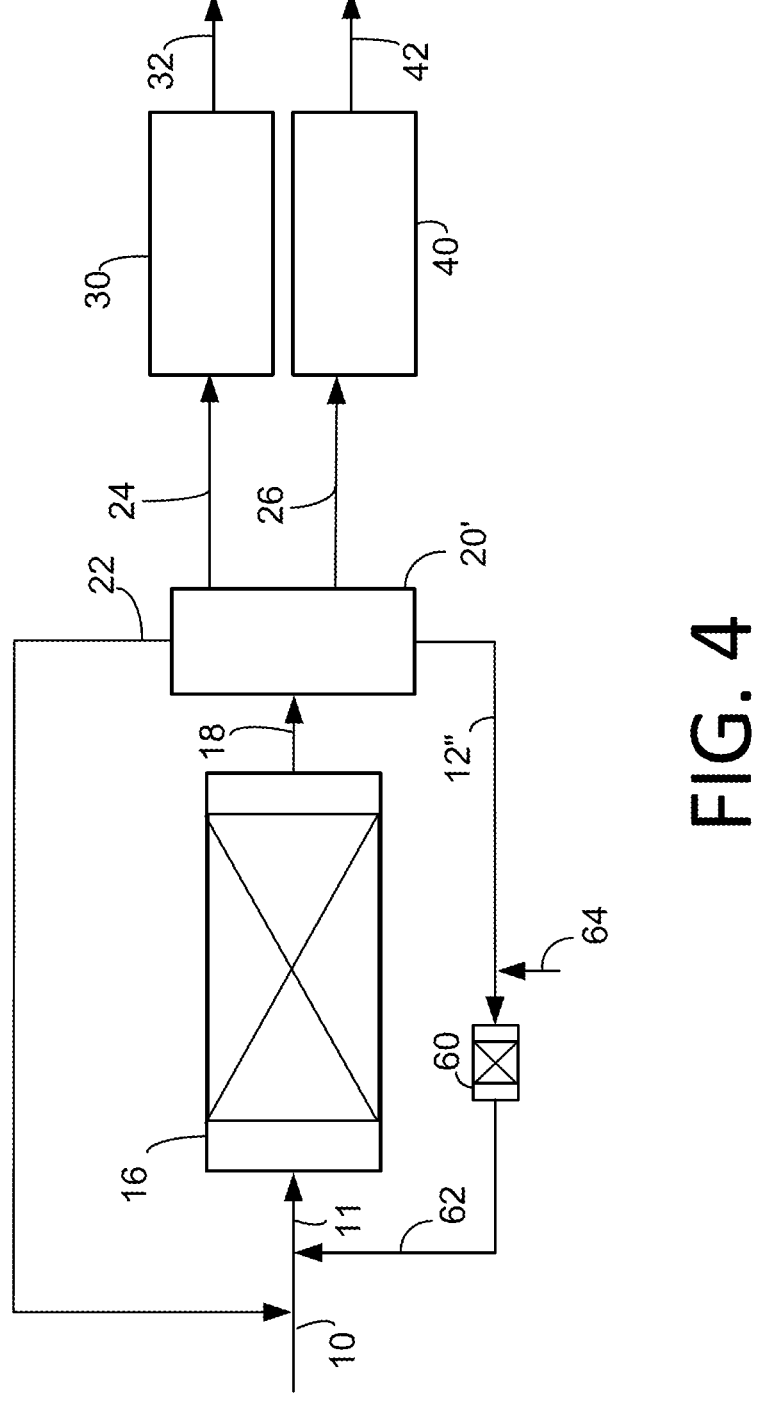
FIG. 4 is a schematic drawing of a process and apparatus of an additional alternative embodiment of FIG. 1.

The heavy paraffin stream in line 12 may also comprise aromatics, benzene, toluene and xylene. FIG. 4 shows an alternative to FIG. 1 which maximizes ethane and propane production by hydrotreating the entire heavy stream in line 12" in a hydrotreating reactor 60 to saturate aromatic rings to naphthenes providing a recycle feed in line 62 to the NEP reactor 16. Elements in FIG. 4 with the same configuration as in FIG. 1 will have the same reference numeral as in FIG. 1. Elements in FIG. 4 which have a different configuration as the corresponding element in FIG. 1 will have the same reference numeral but designated with a double prime symbol ("). The configuration and operation of the apparatus of FIG. 4 is essentially the same as in FIG. 1 with the following exceptions.

The heavy stream in line 12" comprising C4+ paraffins and aromatics, benzene, toluene and xylene is mixed with a hydrogen stream in line 64, heated and charged to the hydrotreating reactor 60.

The hydrotreating reactor 60 may have one or more beds of hydrotreating catalyst to saturate aromatic rings in the heavy stream. The heavy stream may be charged to the hydrotreating reactor 60 at a hydrotreating inlet temperature that may range from about 200° C. (392° F.) to about 400°

C. (752° F.). The hydrotreating reactor 60 may employ interbed hydrogen quench streams if more than one catalyst bed is used.

Suitable hydrotreating catalysts are any known conventional hydrotreating catalysts and include those which are comprised of at least one Group VIII metal, preferably iron, cobalt and nickel, more preferably cobalt and/or nickel and at least one Group VI metal, preferably molybdenum and tungsten, on a high surface area support material, preferably alumina. Other suitable hydrotreating catalysts include zeolitic catalysts, as well as noble metal catalysts where the noble metal is selected from palladium and platinum. It is within the scope of the present description that more than one type of hydrotreating catalyst be used in the same hydrotreating reactor 60. The Group VIII metal is typically present in an amount ranging from about 2 to about 20 wt %, preferably from about 4 to about 12 wt %. The Group VI metal will typically be present in an amount ranging from about 1 to about 25 wt %, preferably from about 2 to about 25 wt %. Generally, hydrotreating conditions include a pressure of about 700 kPa (100 psig) to about 21 MPa (3000 psig). The hydrotreating outlet temperature may range between about 300° C. (572° F.) and about 427° C. (800° F.).

The saturated aromatics and C4+ paraffins in a hydrotreated heavy stream in line 62 may be recycled to join the naphtha stream in line 10 and the hydrogen stream in line 22 and be charged to the NEP reactor 16 in line 11. Hydrogen from the hydrotreating reactor 60 may be recycled with the saturated aromatics to the NEP reactor 16 to reduce or eliminate hydrogen requirements from line 22.

Figure 5:
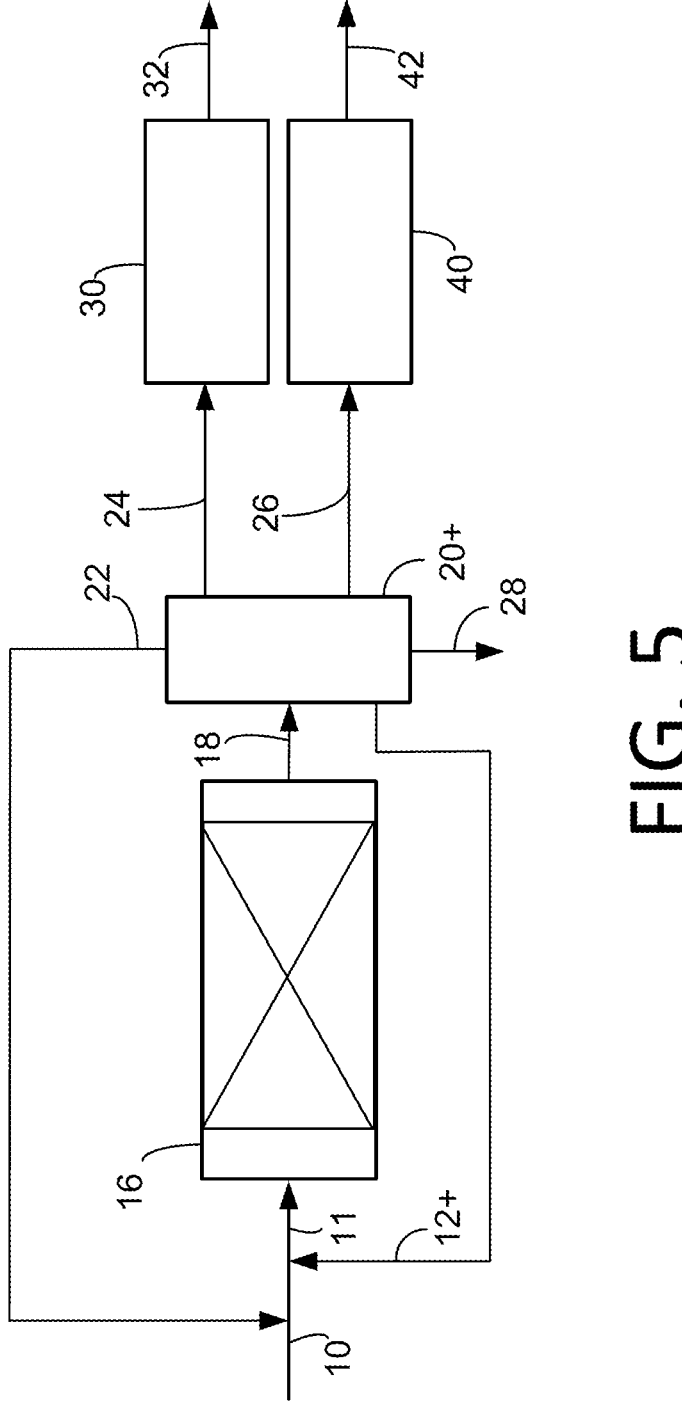
FIG. 5 is a schematic drawing of a process and apparatus of a further alternative embodiment of FIG. 1.

The NEP separation unit 20+ may include a debutanizer column that separates C4 and perhaps C5 hydrocarbons for recycle to the NEP reactor 16 in line 12+ while preserving aromatics for further processing and valorization. FIG. 5 shows an alternative to FIG. 1 which preserves aromatics. Elements in FIG. 5 with the same configuration as in FIG. 1 will have the same reference numeral as in FIG. 1. Elements in FIG. 5 which have a different configuration as the corresponding element in FIG. 1 will have the same reference numeral but designated with a cross symbol (+).

The NEP separation unit 20+ includes a debutanizer column that separates a heavy stream comprising C4 and perhaps C5 paraffins from a depropanizer bottoms stream in a debutanizer overhead line for recycle to the NEP reactor 16 in line 12+ and C5+ or C6+ aromatics in a debutanized bottoms line 28. The aromatics in the debutanized bottoms line 28 may be further processed for valorization of the valuable aromatics.

The present disclosure is further directed to a concept that it is desirable to let a certain fraction of hydrogen and methane slip into an ethane product to reduce separation costs in a naphtha-to-ethane-and-propane process (NEP). Letting a certain fraction of hydrogen and methane slip into an ethane product reduces a total compression power (i.e. refrigeration power) for the NEP process and may require less equipment compared to alternatives.

Letting hydrogen and methane slip into the ethane product also allows for more efficient heat recovery which further reduces energy cost compared to alternatives. The principles of this disclosure have the most benefit when hydrogen and methane in the ethane product have minimal impact on downstream processes. In the case where a downstream process is ethane steam cracking, the ethane feed is diluted with steam to reduce ethane partial pressure in the cracking furnaces. According to a principle of the present disclosure, hydrogen and methane that slip in the NEP process ethane product can partially replace steam in the ethane steam cracker with minimal impact on ethylene yields so long as the volume of hydrogen plus methane is less than or equal to a total volume of steam diluent that would be used for a pure ethane feed.

Typical steam dilution rate in an ethane steam cracker is 0.3 kg steam per kg ethane. This corresponds to 33 volume percent steam to 67 volume percent ethane. According to a principle of the present disclosure, letting hydrogen and methane slip in the NEP process ethane product is advantageous for a volume ratio of ethane to combined hydrogen plus methane of at least 2 before considering ethane recycle.

Ethane steam cracker furnace effluent typically contains unconverted ethane which is recycled back to the ethane cracking reactor. This ethane is further diluted with steam at a typical ratio of 0.3 kg steam per kg ethane recycle. According to a principle of the present disclosure, hydrogen and methane slip in the NEP process ethane product can also displace a portion of steam required for ethane recycle. The steam required for ethane recycle may be as much as two thirds of the steam required for fresh ethane feed. After considering steam required for ethane recycle, letting hydrogen and methane slip in the NEP process ethane product is advantageous for a volume ratio of ethane to combined hydrogen plus methane of at least 1.2.

In some instances, it may be advantageous to replace a portion of steam less than the total desired amount. In these instances, it may be advantageous to let hydrogen and methane slip in the NEP process ethane product for a volume ratio of ethane to combined hydrogen plus methane of at least 1.5.

The main alternatives to the principles of this disclosure are to separate hydrogen from the ethane product using a membrane and recycle compressor, to separate hydrogen and methane from the ethane product using a demethanizer, to separate hydrogen and methane from the ethane product using a chill and flash configuration, or to separate hydrogen and methane from the ethane product using a dividing wall column deethanizer with ethane taken as a side product.

Membranes have been used to selectively remove hydrogen from a hydrocarbon containing stream, but the hydrogen product is produced at low pressure and must be compressed before it can be used for any application other than use as fuel. Employing a recycle compressor adds compression power and capital cost that can be avoided by implementing the principles of the present disclosure.

Alternatively, hydrogen and methane can be separated from the ethane product by chilling and flashing the ethane in several stages and/or separating the hydrogen and methane in a demethanizer. This requires refrigerant at temperatures of −80° C. or lower to achieve good separation. This adds compression power for the refrigeration compressor as well as capital cost for cryogenic heat exchangers.

Dividing wall columns have also been used to achieve ternary separations for less capital cost than could be achieved by performing separations in a stepwise manner. In this case, a dividing wall fractionation column separates propane, ethane, and hydrogen/methane products. Separating hydrogen/methane from ethane requires lower temperature refrigerant in the condenser than would be required for a simple deethanizer separating C2− from propane. Additional refrigeration compression power is required in this scheme compared to letting hydrogen and methane slip in the ethane product.

The current standard practice is to separate ethane from hydrogen and methane at high purity, typically less than 5 weight percent methane and no hydrogen. This corresponds to a volume ratio of ethane to combined hydrogen plus methane of greater than 10. Depending on the molar ratio of hydrogen, methane, and ethane in the feed, the current standard practice can be achieved by the main alternatives to the principles of this disclosure described above.

The principle of the present disclosure to slip hydrogen and methane into the ethane product have the most benefit when this reduces separation cost in the NEP process. This advantage can occur when ethane is purified to a lower purity than the standard practice. A reduction in separations cost can be achieved when the volume ratio of ethane to combined hydrogen plus methane is less than or equal to 10, more preferably when the volume ratio is less than or equal to 8, and most preferably when the volume ratio is less than or equal to 5.

Figure 6:
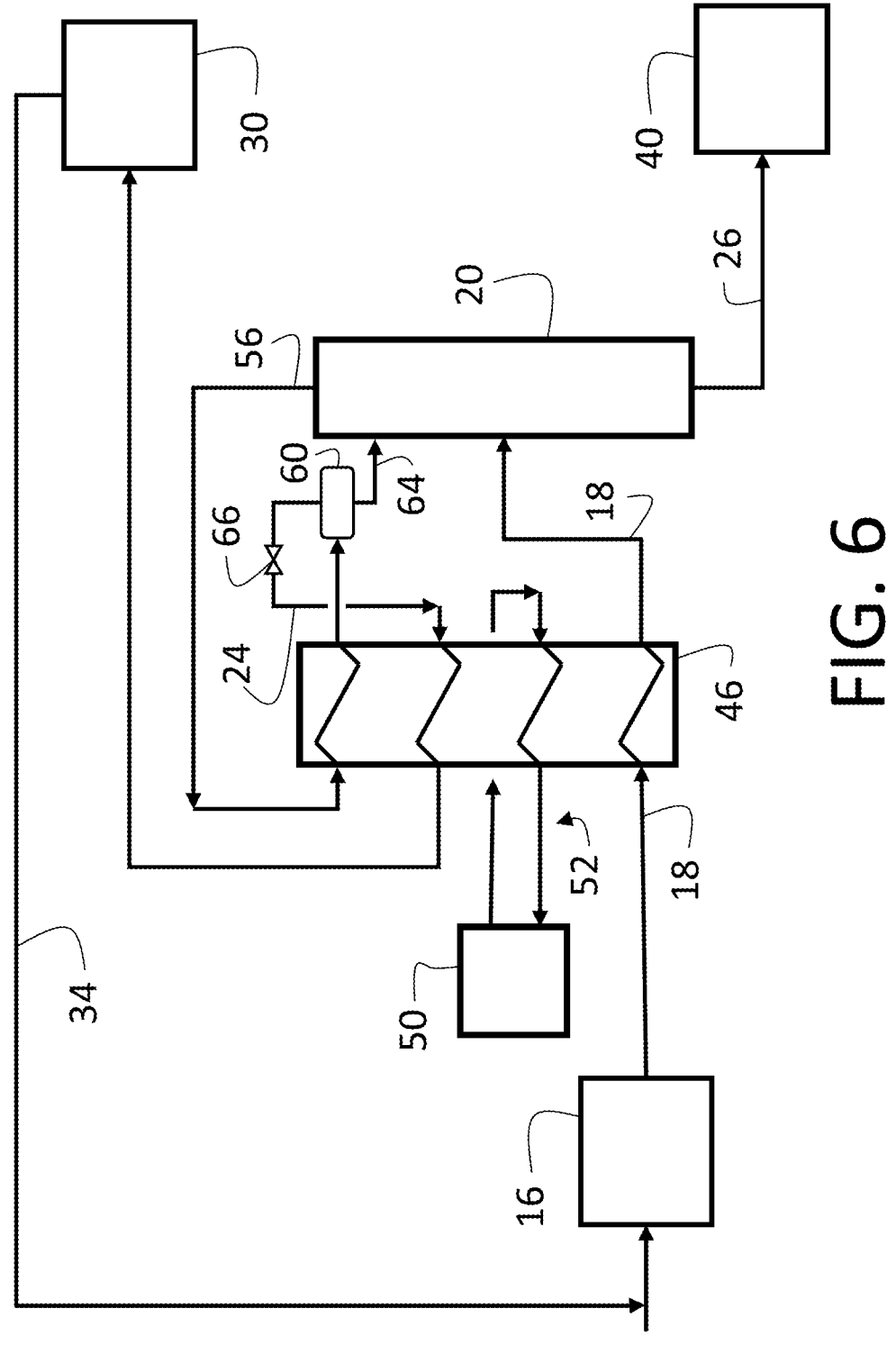
FIG. 6 is a schematic drawing of a process and apparatus of the present disclosure showing a slip stream according to the present disclosure.
Figure 7:
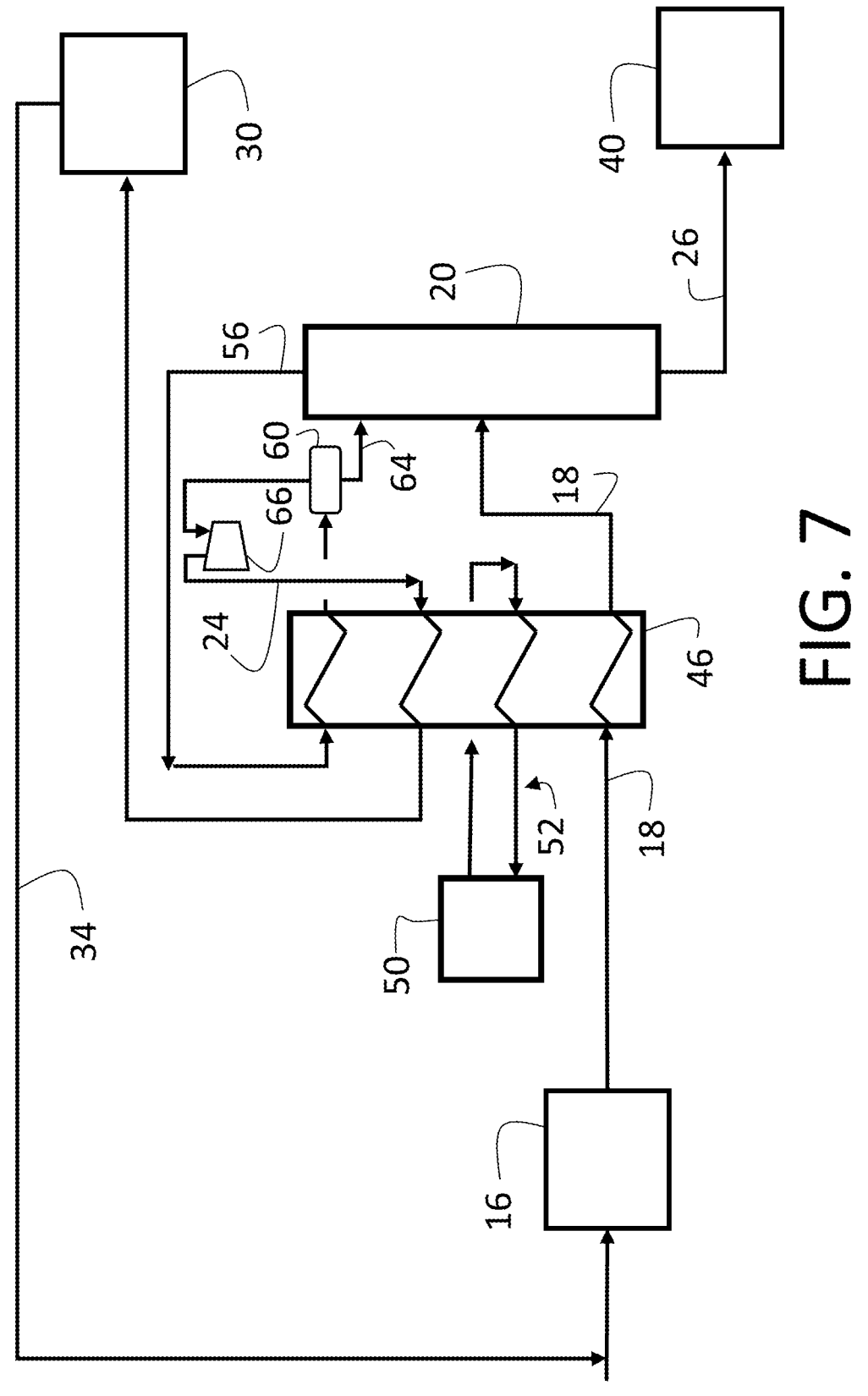
FIG. 7 is a schematic drawing of an alternative process and apparatus to the process and apparatus according to FIG. 6.

Referring to FIGS. 6 and 7, in a process and apparatus for making ethylene and propylene from a hydrocarbon feed, a naphtha stream is contacted with a catalyst in the NEP reactor 16 to pass a light paraffin effluent in line 18 to a coldbox 46. Refrigeration unit 50 passes a refrigerating fluid in line 52 to maintain the desired temperature in the coldbox 46 to about −20° C. The coldbox 46 may be a multi-stream heat exchanger.

The effluent stream is a hydrocarbon stream, comprising hydrogen, and C1 to C6+ hydrocarbons, preferably comprising ethane, hydrogen, and/or methane and hydrocarbons with 3 or greater carbons. It is cooled in the coldbox 46 and passed via line 18 to an NEP separator 20, such as a deethanizer as feed. The hydrocarbon stream is separated into a bottom product, comprising propane and other heavy hydrocarbons with 3 or more carbons. It may be passed directly in line 26 to propylene producing unit 40 or separated further into a heavy hydrocarbon stream containing C4+ hydrocarbons and a propane-rich stream which is passed in line 26 to propylene producing unit 40.

The NEP separator 20 also produces an overhead product comprising hydrogen and hydrocarbons with 2 or less carbons, preferably an ethane-rich stream comprising hydrocarbons with 2 or less carbons. The overhead product passes within line 56 to and through the coldbox 46 to condense a portion of the overhead product. Coldbox 46 acts as the condenser for the overhead product in line 56, and block 60 is a condenser receiver (also known as a reflux drum). The two phase overhead product then passes through the condenser receiver 60. A liquid stream drops out of the condenser receiver 60 and is returned to the NEP separator 20 via line 64.

An ethane-rich stream, comprising hydrogen and hydrocarbons with 2 or less carbons, preferably ethane, hydrogen, and methane, exits the condenser receiver 60 via line 24. The ethane stream may be fed via line 24 downstream to a process which produces ethylene from the ethane-rich stream, such as an ethylene producing unit 30, for example a downstream ethane steam cracker or ethane oxidative dehydrogenation process. The molar ratio of ethane to hydrogen plus methane (ethane:(hydrogen+methane) is important in this ethane-rich stream for the invention. The molar ratio should be at least 1.2, preferably at least 1.5, more preferably at least 1.8, and most preferably 2.0. At a molar ratio of at least 2.0, the hydrogen and methane replace all steam diluent for the ethane feed before considering ethane recycle. A greater benefit is achieved when the molar ratio is greater than 2.0 since then some steam diluent can be fed to the ethane cracking furnace without increasing the size of the ethane cracking furnace. At a molar ratio of 2.4, the hydrogen and methane replace two-thirds of the steam diluent for the ethane feed before considering ethane recycle. Some steam is beneficial to the ethane steam cracker to prevent coke buildup. The ethane steam cracker furnace effluent contains unreacted ethane which may be recycled back to the ethane steam cracking furnace. This recycle ethane is also typically diluted with steam to maintain a preferred ethane partial pressure. This extra dilution steam may also be replaced by hydrogen and methane in the ethane-rich stream in line 24. At an ethane to combined hydrogen and methane molar ratio of 1.2, the hydrogen and methane replace all steam diluent for both the fresh feed and ethane recycle. A greater benefit is achieved when the molar ratio is greater than 1.2 since then some steam diluent can be fed to the ethane cracking furnace without increasing the size of the ethane cracking furnace.

A pressure control device or pressure letdown device 66 is located within line 24 downstream from the condenser receiver 60 and upstream from the multi-stream heat exchanger coldbox 46. One purpose of the pressure letdown device 66 is to enhance heat recovery by first decreasing pressure of stream 24 which decreases the temperature of stream 24 as the gas expands, then recovering additional heat in a heat exchanger. Thus, the ethane-rich stream overhead product is passed through the pressure letdown device 66 followed by a heat recovery device, such as a heat exchanger, for example the multi-stream heat exchanger coldbox 46. This process recovers heat which provides some of the cooling duty to condense a portion of the deethanizer overhead in line 56.

The pressure letdown device 66 may be a valve (see FIG. 6) or a turbine, such as a turbo-expander (see FIG. 7). The pressure letdown device 66 is placed before the ethane-rich stream heat recovery exchanger so that more heat can be extracted from the ethane-rich stream which reduces net refrigeration needs. Combining hydrogen and methane slip into the ethane-rich stream can be combined with the pressure letdown device 66 to reduce utilities.

As described above, the pressure letdown device 66, may be a recovery turbine, such as a turbo-expander. A turbo-expander is a centrifugal or axial-flow turbine, through which a high-pressure gas is expanded to produce work that is often used to drive a compressor or generator. Here, the turbo-expander may partially liquefy the ethane-rich stream. Work recovered from the turbo-expander plus heat recovered from the partially liquefied ethane-rich stream in line 24 in a heat recovery device such as the multi-stream heat exchanger coldbox 46 may reduce utilities more than if the pressure letdown device 66 is a valve. One purpose of the valve/turbine in the examples is to enhance heat recovery by first decreasing pressure then recovering additional heat in a heat exchanger.

This proposed scheme saves energy and some equipment compared to the alternatives while not increasing the size of the downstream ethane steam cracking furnaces of the ethylene producing unit 30. Table 1 shows a comparison of the saving between the pressure letdown valve of FIG. 6, the pressure letdown turbine of FIG. 7, and alternative solutions.

TABLE 1

| Energy Savings by Process | | | | | |
| --- | --- | --- | --- | --- | --- |
| Compression Duty | | H2 Slip Letdown Valve | H2 Slip Turbine | Chill and Flash after DEC2 | H2 Membrane after DEC2 |
| Propylene Refrig. Compressor | kW | 6304 | 5254 | 6604 | 6991 |
| Ethylene Refrig. Compressor | kW | 0 | 0 | 512 | 0 |
| Turbo-expander | kW | 0 | −1651 | −432 | 0 |
| Total | kW | 6304 | 3603 | 6684 | 6991 |

The term "communication" means that fluid flow is operatively permitted between enumerated components, which may be characterized as "fluid communication".

The term "downstream" means that at least a portion of fluid flowing to the subject in downstream communication may operatively flow from the object with which it fluidly communicates.

The term "upstream" means that at least a portion of the fluid flowing from the subject in upstream communication may operatively flow to the object with which it fluidly communicates.

The term "direct communication" means that fluid flow from the upstream component enters the downstream component without passing through any other intervening vessel.

The term "indirect communication" means that fluid flow from the upstream component enters the downstream component after passing through an intervening vessel.

The term "bypass" means that the object is out of downstream communication with a bypassing subject at least to the extent of bypassing.

The term "reflux" means liquid condensed from the overhead vapor of a distillation column and returned to the top of the column.

As used herein, the term "predominant" or "predominate" means greater than 50%, suitably greater than 75% and preferably greater than 90%.

As used herein, the term "rich" is defined as at least 50 mol %.

While the specific embodiments have been illustrated and described, numerous modifications come to mind without significantly departing from the spirit of the invention, and the scope of protection is only limited by the scope of the accompanying Claims.

SPECIFIC EMBODIMENTS

While the following is described in conjunction with specific embodiments, it will be understood that this description is intended to illustrate and not limit the scope of the preceding description and the appended claims.

A first embodiment of the invention is a process for making ethylene from a hydrocarbon feed comprising separating the hydrocarbon feed comprising ethane, hydrogen, and/or methane and hydrocarbons with 3 or greater carbons into an ethane-rich stream comprising hydrocarbons with 2 or less carbons and a heavy stream comprising hydrocarbons with 3 or more carbons; and passing the ethane-rich stream to a process which produces ethylene, wherein the ethane-rich stream has an ethane to combined hydrogen and methane molar ratio of at least 1.2 and less than or equal to 10. An embodiment of the invention is one, any or all of prior embodiments in this paragraph up through the first embodiment in this paragraph further comprising separating the hydrocarbon feed in a deethanizer upstream of the process which produces ethylene, wherein the deethanizer outputs a propane stream as a bottom product and an overhead product, wherein the overhead product comprises ethane, hydrogen, and methane. An embodiment of the invention is one, any or all of prior embodiments in this paragraph up through the first embodiment in this paragraph further comprising passing the overhead product through a condenser receiver and sending a liquid back to the deethanizer as reflux and passing the ethane-rich stream to the process which produces ethylene. An embodiment of the invention is one, any or all of prior embodiments in this paragraph up through the first embodiment in this paragraph wherein the ethane-rich stream is passed through a pressure letdown device followed by a heat recovery device. An embodiment of the invention is one, any or all of prior embodiments in this paragraph up through the first embodiment in this paragraph wherein the heat recovery device is a heat exchanger which provides a portion of a cooling duty to condense a portion of the overhead product of the deethanizer. An embodiment of the invention is one, any or all of prior embodiments in this paragraph up through the first embodiment in this paragraph wherein the pressure letdown device is a valve. An embodiment of the invention is one, any or all of prior embodiments in this paragraph up through the first embodiment in this paragraph wherein the pressure letdown device is a turbine. An embodiment of the invention is one, any or all of prior embodiments in this paragraph up through the first embodiment in this paragraph wherein the turbine is a turbo-expander which partially liquefies the ethane-rich stream. An embodiment of the invention is one, any or all of prior embodiments in this paragraph up through the first embodiment in this paragraph wherein the hydrocarbon feed is derived from naphtha in an upstream process. An embodiment of the invention is one, any or all of prior embodiments in this paragraph up through the first embodiment in this paragraph wherein the molar ratio is at least 1.5. An embodiment of the invention is one, any or all of prior embodiments in this paragraph up through the first embodiment in this paragraph wherein the molar ratio is at least 1.8. An embodiment of the invention is one, any or all of prior embodiments in this paragraph up through the first embodiment in this paragraph wherein the molar ratio is at least 2.0. An embodiment of the invention is one, any or all of prior embodiments in this paragraph up through the first embodiment in this paragraph wherein the molar ratio is less than or equal to 8. An embodiment of the invention is one, any or all of prior embodiments in this paragraph up through the first embodiment in this paragraph wherein the molar ratio is less than or equal to 5.

A second embodiment of the invention is an apparatus for separating naphtha into ethylene and propylene comprising a source of a first fluid feed to an ethane steam cracker, the first fluid feed being an ethane-rich stream comprising a molar ratio of ethane to combined hydrogen and methane in the fluid feed is at least 1.2 and less than or equal to 10; and a pressure letdown device wherein the pressure letdown device first decreases pressure of the ethane-rich stream which decreases a temperature of the ethane-rich stream as a gas of the ethane-rich stream expands, then recovers heat in a heat exchanger. An embodiment of the invention is one, any or all of prior embodiments in this paragraph up through the second embodiment in this paragraph further comprising a deethanizer, wherein the deethanizer outputs an overhead product to the heat exchanger, and wherein the overhead product comprises ethane, hydrogen, and methane, and wherein optionally a propane-rich is sent to a propane dehydrogenation unit to make propylene. An embodiment of the invention is one, any or all of prior embodiments in this paragraph up through the second embodiment in this paragraph further comprising a condenser receiver which receives the overhead product from the heat exchanger and passes the ethane-rich stream to the pressure letdown device, wherein the pressure letdown device receives the ethane-rich stream from the condenser. An embodiment of the invention is one, any or all of prior embodiments in this paragraph up through the second embodiment in this paragraph wherein the pressure letdown device is one of a valve or a turbine, and the first fluid feed is passed by the pressure letdown device to the heat exchanger prior to the ethane steam cracker. An embodiment of the invention is one, any or all of prior embodiments in this paragraph up through the second embodiment in this paragraph wherein the molar ratio is at least 1.5. An embodiment of the invention is one, any or all of prior embodiments in this paragraph up through the second embodiment in this paragraph wherein the molar ratio is at least 1.8. An embodiment of the invention is one, any or all of prior embodiments in this paragraph up through the second embodiment in this paragraph wherein the molar ratio is at least 2.0. An embodiment of the invention is one, any or all of prior embodiments in this paragraph up through the first embodiment in this paragraph wherein the molar ratio is less than or equal to 8. An embodiment of the invention is one, any or all of prior embodiments in this paragraph up through the first embodiment in this paragraph wherein the molar ratio is less than or equal to 5.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process for making ethylene from a hydrocarbon feed comprising:

separating the hydrocarbon feed comprising ethane, hydrogen, methane and hydrocarbons with 3 or greater carbons into an ethane-rich stream comprising hydrocarbons with 2 or less carbons and a heavy stream comprising hydrocarbons with 3 or more carbons; and passing the ethane-rich stream to an ethane steam cracker or ethane oxidative dehydrogenation process which produces ethylene, wherein the ethane-rich stream has an ethane to combined hydrogen and methane molar ratio of at least 1.2 and less than or equal to 10.

2. The process of claim 1 further comprising separating the hydrocarbon feed in a deethanizer upstream of the process which produces ethylene, wherein the deethanizer outputs a propane stream as a bottom product and an overhead product, wherein the overhead product comprises ethane and at least one of hydrogen or methane.

3. The process of claim 2 further comprising passing the overhead product through a condenser receiver and sending a liquid back to the deethanizer as reflux and passing the ethane-rich stream to the process which produces ethylene.

4. The process of claim 3 wherein the ethane-rich stream is passed through a pressure letdown device followed by a heat recovery device.

5. The process of claim 4 wherein the heat recovery device is a heat exchanger which provides a portion of a cooling duty to condense a portion of the overhead product of the deethanizer.

6. The process of claim 5 wherein the pressure letdown device is a valve.

7. The process of claim 5 wherein the pressure letdown device is a turbine.

8. The process of claim 7 wherein the turbine is a turbo-expander which partially liquefies the ethane-rich stream.

9. The process of claim 1 wherein the hydrocarbon feed is derived from naphtha in an upstream process.

10. The process of claim 1 wherein the molar ratio is at least 1.5.

11. The process of claim 1 wherein the molar ratio is at least 1.8.

12. The process of claim 1 wherein the molar ratio is at least 2.0.

13. The process of claim 1 wherein the molar ratio is less than 8.

14. The process of claim 1 wherein the molar ratio is less than 5.

* * * * *